(12) United States Patent
Muzaffar et al.

(10) Patent No.: US 11,125,635 B2
(45) Date of Patent: Sep. 21, 2021

(54) SENSOR ARRAY FOR CONSOLIDATED FORCE MEASUREMENT

(71) Applicant: Khalifa University of Science and Technology, Abu Dhabi (AE)

(72) Inventors: Shahzad Muzaffar, Abu Dhabi (AE); Ibrahim Elfadel, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 301 days.

(21) Appl. No.: 16/023,335

(22) Filed: Jun. 29, 2018

(65) Prior Publication Data
US 2020/0003643 A1  Jan. 2, 2020

(51) Int. Cl.
*G01L 5/00* (2006.01)
*A61B 5/103* (2006.01)
*A61B 5/00* (2006.01)
*A43B 3/00* (2006.01)

(52) U.S. Cl.
CPC .......... *G01L 5/0052* (2013.01); *A43B 3/0005* (2013.01); *A61B 5/1036* (2013.01); *A61B 5/6807* (2013.01); *G01L 5/0038* (2013.01); *A61B 2562/0247* (2013.01); *A61B 2562/046* (2013.01)

(58) Field of Classification Search
CPC ... G01L 5/0052; G01L 5/0038; A43B 3/0005; A43B 13/223; A61B 5/1036; A61B 5/6807; A61B 2562/046; A61B 2562/0247
See application file for complete search history.

(56) References Cited

U.S. PATENT DOCUMENTS

| 6,155,120 | A  | * | 12/2000 | Taylor       | A61B 5/1036 73/862.046 |
| 6,505,522 | B1 | * | 1/2003  | Wilssens     | A61B 5/1036 73/862.51 |
| 7,426,873 | B1 | * | 9/2008  | Kholwadwala  | A43B 3/00 73/777 |
| 2008/0201987 | A1 | * | 8/2008 | Bell | A43B 7/34 36/84 |

(Continued)

OTHER PUBLICATIONS

Bamberg, Stacy, et al., "Gait Analysis Using a Shoe-Integrated Wireless Sensor System," IEEE Transactions on Information Technology in Biomedecine, vol. 12, Issue 4, Jul. 2008, IEEE, pp. 413-423.

*Primary Examiner* — Suman K Nath
(74) *Attorney, Agent, or Firm* — Withrow & Terranova, PLLC (57) ABSTRACT

A method includes the steps of providing a number of force consolidators between an object and a surface, providing a number of force sensors, each in a different one of the force consolidators, measuring an output of the force sensors, and processing the output of the force sensors to determine a total force exerted between the object and the surface. The force consolidators are each configured to reduce a portion of a surface area of the object into a consolidated surface area such that forces exerted on the portion of the surface area are concentrated in the consolidated surface area. By using the force consolidators along with the force sensors, the total force exerted by the object on the surface may be easily measured using off-the-shelf force sensor technologies.

20 Claims, 7 Drawing Sheets

(56) References Cited

U.S. PATENT DOCUMENTS

| | | | | |
|---|---|---|---|---|
| 2008/0306410 A1* | 12/2008 | Kalpaxis | .............. | A61B 5/1038 600/592 |
| 2013/0333094 A1* | 12/2013 | Rogers | ................. | A61N 1/0476 2/161.7 |
| 2017/0127749 A1* | 5/2017 | Boeck | ....................... | A43B 7/32 |

* cited by examiner

SENSOR ARRAY FOR CONSOLIDATED FORCE MEASUREMENT

FIELD OF THE DISCLOSURE

The present disclosure relates to sensor arrays for accurately measuring force, and specifically to sensor arrays designed to integrate with a shoe for the accurate measurement of forces exerted between a foot and a walking surface.

BACKGROUND

Figure 1A:
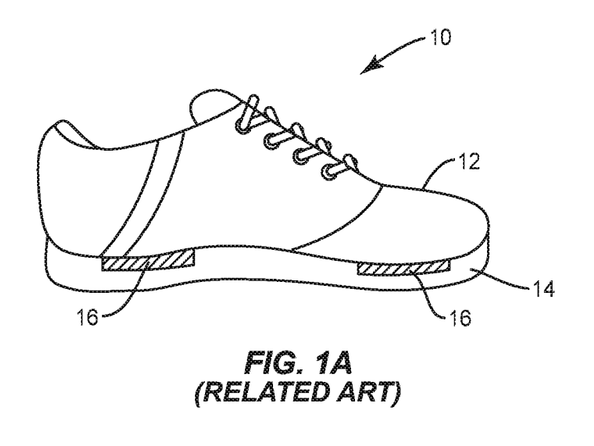
FIG. 1A shows a conventional shoe for measuring a force exerted by a foot on a walking surface.

It is often desirable to accurately measure the force exerted between a foot and a walking surface. These force measurements may be used, for example, to assess the gait of a person, animal, robot, or the like. Conventionally, these force measurements have been made by placing a number of force sensors in a shoe that is placed on a foot such that the force sensors reside between the foot and a walking surface. An exemplary diagram illustrating this conventional approach is shown in FIG. 1A, which shows a shoe 10 including a shoe upper 12, an insole 14 attached to the shoe upper 12, and a number of force sensors 16 embedded in the insole 14. The force sensors 16 use any number of transduction mechanisms to convert a force exerted by a foot provided in the shoe 10 on a walking surface into a measurable electrical signal. The force sensors 16 have conventionally been off-the-shelf parts, which are provided in a number of predefined sizes. Accordingly, the force sensors 16 are only provided in a subset of the surface area of the insole, and thus only measure a portion of the force exerted by a foot provided in the shoe 10 on a walking surface.

Figure 1B:
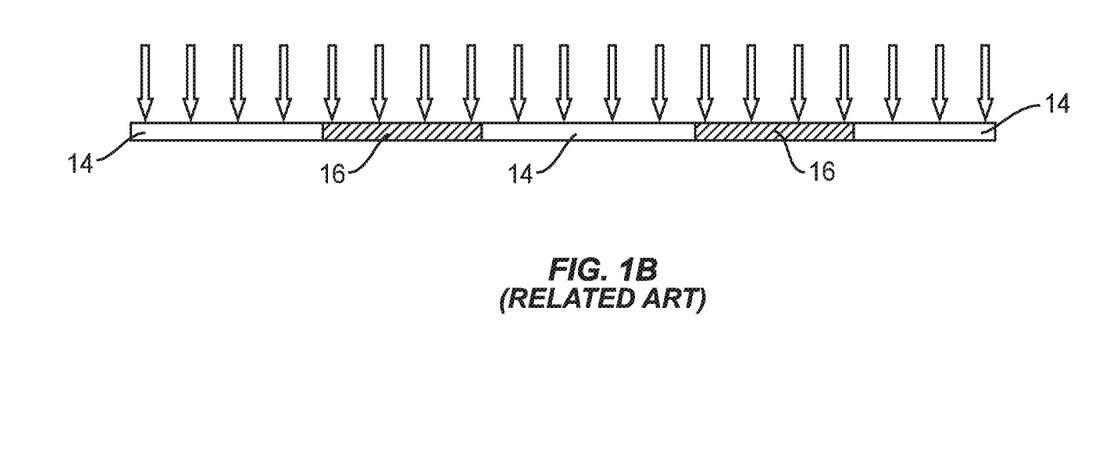
FIG. 1B shows a cross-section of an insole of the shoe shown in FIG. 1A.

The force exerted by a foot on a walking surface is distributed over an entire surface area of the foot (and, by extension, the entire surface of the shoe 10 when placed on the foot) in contact with the walking surface as illustrated in FIG. 1B, which shows a cross-sectional view of the insole 14 including the force sensors 16. The arrows in FIG. 1B represent the force exerted by a foot in the shoe 10 on a walking surface. Due to the size of the force sensors 16 (i.e., due to the fact that the force sensors 16 are only provided in a subset of the surface area of the insole 14), the force exerted by the foot is only measured within the area occupied by the force sensors 16. Since the force exerted by the foot is spread out over the surface area of the insole 14, the total force exerted by the foot on the walking surface is not measured by the force sensors 16. It is difficult to extrapolate the total force exerted by the foot when measuring in this way, because the force applied by the foot will be different at different points of contact between the foot and the walking surface. While custom force sensors that cover the entirety of insole 14 may be used to correct this problem, such force sensors are expensive and not readily available. Accordingly, there is a need for a way to accurately measure the force exerted between a foot and a walking surface.

SUMMARY

In one embodiment, a method includes the steps of providing a number of force consolidators between an object and a surface, providing a number of force sensors, each in a different one of the force consolidators, measuring an output of the force sensors, and processing the output of the force sensors to determine a total force exerted between the object and the surface. The force consolidators are each configured to reduce a portion of a surface area of the object into a consolidated surface area such that forces exerted on the portion of the surface area are concentrated in the consolidated surface area. By using the force consolidators along with the force sensors, the total force exerted by the object on the surface may be easily measured using off-the-shelf force sensor technologies.

In one embodiment, an apparatus includes a number of force consolidators, a number of force sensors, and force determination circuitry. The force consolidators are configured to be provided between an object and a surface such that each of the force consolidators reduces a portion of a surface area of the object into a consolidated surface area at the surface so that forces exerted on the portion of the surface area are concentrated in the consolidated surface area. Each one of the force sensors is provided between the object and the surface in a different one of the force consolidators. The force determination circuitry is configured to process an output of each one of the force sensors to determine a total force exerted between the object and the surface. By using the force consolidators along with the force sensors, the total force exerted by the object on the surface may be easily measured using off-the-shelf force sensors.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 2A:
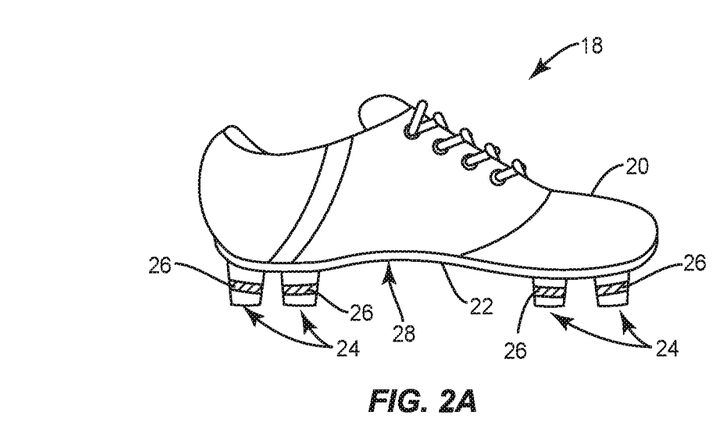
FIG. 2A shows a shoe for measuring a force exerted by a foot on a walking surface according to one embodiment of the present disclosure.

As discussed above, there is a need to accurately measure the force exerted between a foot and a walking surface. Accordingly, FIG. 2A shows a shoe 18 for accurately measuring the force exerted between a foot provided in the shoe 18 and a walking surface according to one embodiment of the present disclosure. The shoe 18 includes a shoe upper 20, an insole 22 attached to the shoe upper 20, a number of force consolidators 24 coupled to the insole 22, and a number of force sensors 26, each one of the force sensors 26 in a different one of the force consolidators 24. In particular, the force consolidators 24 are provided on a bottom surface 28 of the insole 22 and reduce a surface area of the bottom surface 28 into a consolidated surface area, which is configured to be in contact with a walking surface on which the shoe 18 is provided. In other words, the force consolidators 24 reduce a total surface area of the shoe 18 that would normally contact a walking surface such that all of the force exerted by a foot provided in the shoe 18 on the walking surface must be transferred through the force consolidators 24. Because the dimensions of the force consolidators 24 can be easily controlled, the force sensors 26 provided in the force consolidators 24 may measure a total force exerted by a foot provided in the shoe 18 on a walking surface as discussed in detail below.

Figure 2B:
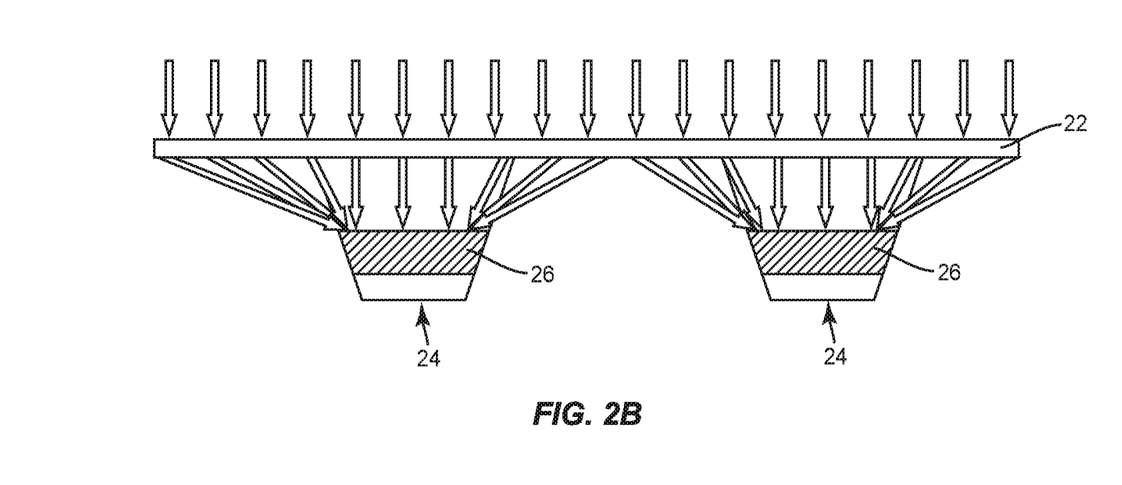
FIG. 2B shows a cross-section of an insole of the shoe shown in FIG. 2A according to one embodiment of the present disclosure.

FIG. 2B shows a cross-sectional view of the insole 22 and the force consolidators 24 according to one embodiment of the present disclosure. The arrows in FIG. 2B represent the force exerted by a foot in the shoe 18 on a walking surface. As shown, the force consolidators 24 effectively consolidate the entire force exerted by the foot into a small surface area such that the entire force is transferred to the walking surface via the force consolidators 24. By placing the force sensors 26 in the force consolidators 24, the force sensors 26 can measure the total force exerted by the foot on the walking surface. Because the force consolidators 24 can be provided in any number of sizes, they can be sized such that the force sensors 26 are able to be sandwiched between two layers thereof, as discussed below, which, as discussed above, allows the force sensors 26 to measure the entirety of the force exerted by the foot on a walking surface without requiring custom sensor technologies.

Figure 2C:
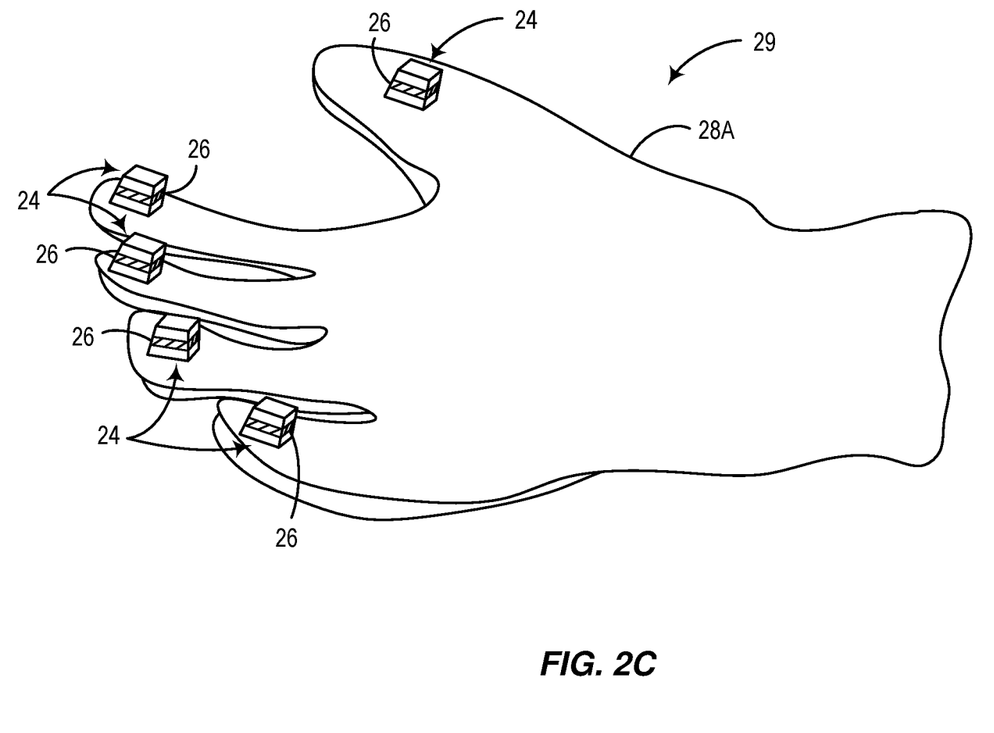
FIG. 2C shows a glove for measuring a force exerted by a hand in contact with a held object according to one embodiment of the present disclosure.

While shown in the context of a shoe above, the principles of the present disclosure may be incorporated in any number of different objects that may be worn or otherwise positioned between a subject and a surface against which force is desired to be measured. For example, as shown in FIG. 2C, the force consolidators 24 discussed herein may be attached to a glove 29 worn on the hand such that the force consolidators 24 reduce a total surface area along a bottom surface 28A of the glove 29 normally in contact with a held object.

Figures 3A, 3B, 3C:
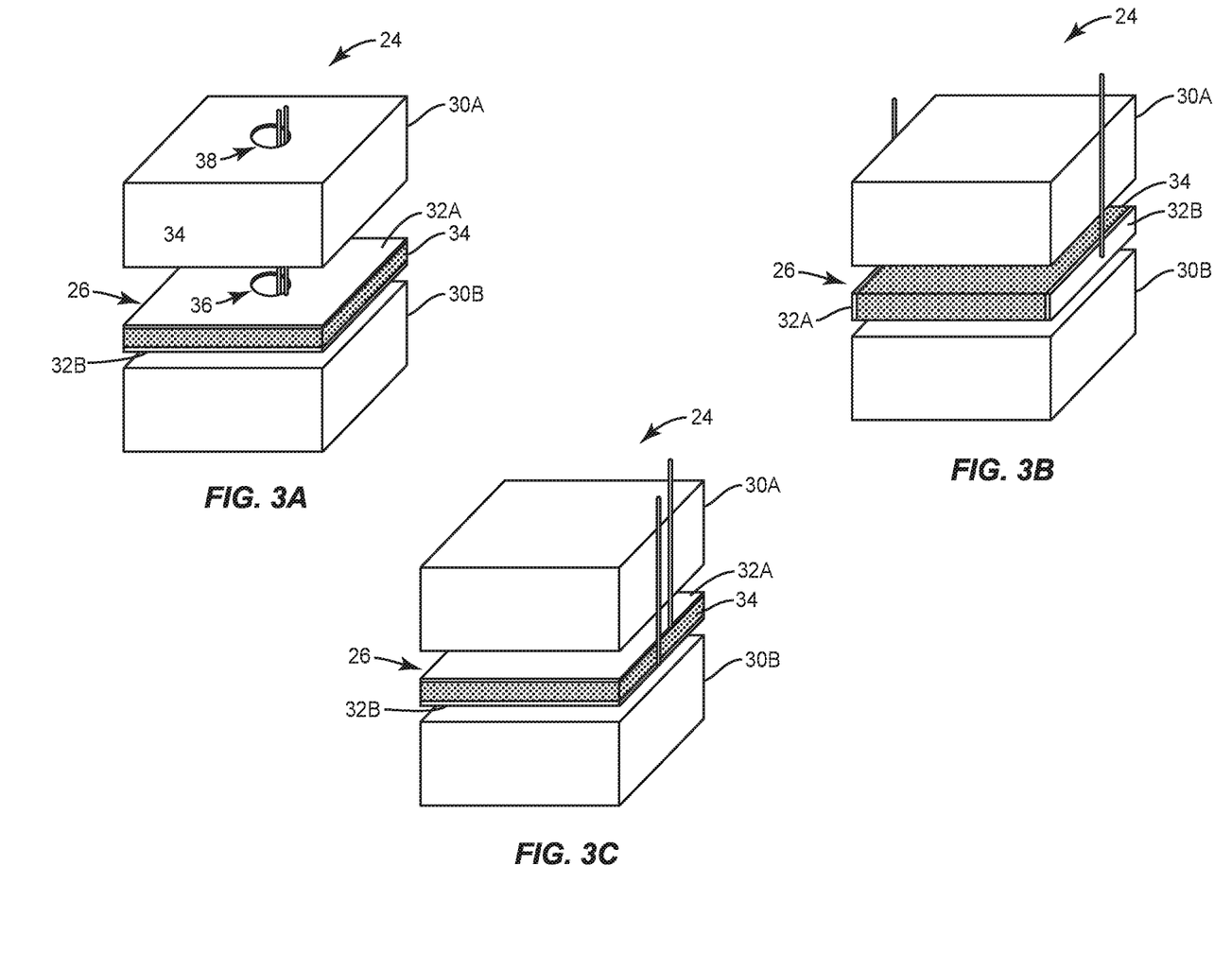
FIGS. 3A through 3C show an exploded view of a force consolidator including a force sensor according to various embodiments of the present disclosure.

FIG. 3A shows an exploded view of a force consolidator 24 and a force sensor 26 in the force consolidator 24 according to one embodiment of the present disclosure. As shown, the force consolidator 24 may include an upper force consolidator layer 30A and a lower force consolidator layer 30B. The force sensor 26 may be sandwiched between the upper force consolidator layer 30A and the lower force consolidator layer 30B such that the force sensor 26 bisects the upper force consolidator layer 30A and the lower force consolidator layer 30B. That is, the force sensor 26 may be provided edge-to-edge between the upper force consolidator layer 30A and the lower force consolidator layer 30B so that the force sensor 26 measures the entirety of a force provided via the force consolidator 24. The force sensor 26 may include a first electrode 32A, a second electrode 32B, and a transducer 34 between the first electrode 32A and the second electrode 32B. The first electrode 32A and the transducer 34 may include an opening 36 such that a wire from the second electrode 32B may pass through the opening 36. The upper force consolidator layer 30A may also include an opening 38 such that a wire from both the first electrode 32A and the second electrode 32B pass through the opening, and may ultimately be routed to circuitry for measuring an electrical output from the force sensor 26.

FIG. 3B shows a force consolidator 24 and force sensor 26 according to an additional embodiment of the present disclosure. The force consolidator 24 and force sensor 26 shown in FIG. 3B are similar to that shown in FIG. 3A, except that neither the upper force consolidator layer 30A nor the force sensor 26 include any openings. Additionally, the first electrode 32A and the second electrode 32B are provided on outer edges of the transducer 34, rather than above and below it as shown in FIG. 3A. Wires from the first electrode 32A and the second electrode 32B are routed externally to the force consolidator 24 along outer edges thereof.

FIG. 3C shows the force consolidator 24 and the force sensor 26 according to yet another embodiment of the present disclosure. The force consolidator 24 and force sensors 26 shown in FIG. 3C are similar to that shown in FIG. 3B, except that the first electrode 32A and the second electrode 32B are provided on the top and bottom of the transducer 34, respectively. Wires for the first electrode 32A and the second electrode 32B are still routed externally to the force consolidator 24 along outer edges thereof.

The transducer 34 in the force sensor 26 may be any type of transducer capable of transducing a mechanical force applied thereto into an electrical signal. In one embodiment, the transducer 34 is a resistive transducer that varies a resistance between the first electrode 32A and the second electrode 32B in proportion to a force applied thereto. In another embodiment, the transducer 34 is a capacitive transducer that varies a capacitance between the first electrode 32A and the second electrode 32B in proportion to a force applied thereto. Those skilled in the art will appreciate that the transducer 34 may comprise several different types of transducer, all of which are contemplated herein.

Figure 4:
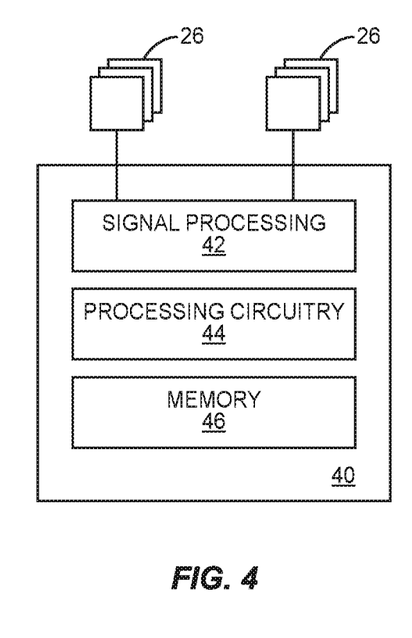
FIG. 4 shows force determination circuitry according to one embodiment of the present disclosure.

In order to measure and process force measurements from the force sensors 26, the force sensors 26 may be coupled to force determination circuitry 40 as illustrated in FIG. 4. As shown, any number of force sensors 26 may be connected to signal processing circuitry 42 within the force determination circuitry 40. The signal processing circuitry 42 may perform any necessary conversion, correction, or other processing, on force measurements form the force sensors 26, and may be connected to processing circuitry 44. The processing circuitry 44 may execute instructions stored in a memory 46 coupled thereto in order to determine a total force exerted between a foot and a walking surface based on the force measurements.

Specifically, the signal processing circuitry 42 may normalize an electrical signal from each one of the force sensors 26 and perform an analog to digital conversion thereon. The processing circuitry 44 may apply a conversion model for converting the digital signals from the signal processing circuitry 42 into a total force measurement. This conversion model may be based on parameters of the force sensors 26 provided by a manufacturer thereof, or may be experimentally determined. In the course of designing and testing the inventions discussed herein, the inventors discovered a non-linear relationship between the force applied to the force sensors 26 and the electrical readings provided therefrom. Accordingly, in some embodiments the processing circuitry 44 may us a non-linear conversion model for determining the total force. For example, the processing circuitry 44 may make an initial determination of the total force based on the electrical signals provided by the force sensors 26 and specifications for the force sensors 26 provided by the manufacturer thereof. The processing circuitry 44 may then apply a division factor to the initial determination of the total force in order to determine an actual total force.

Figure 5:
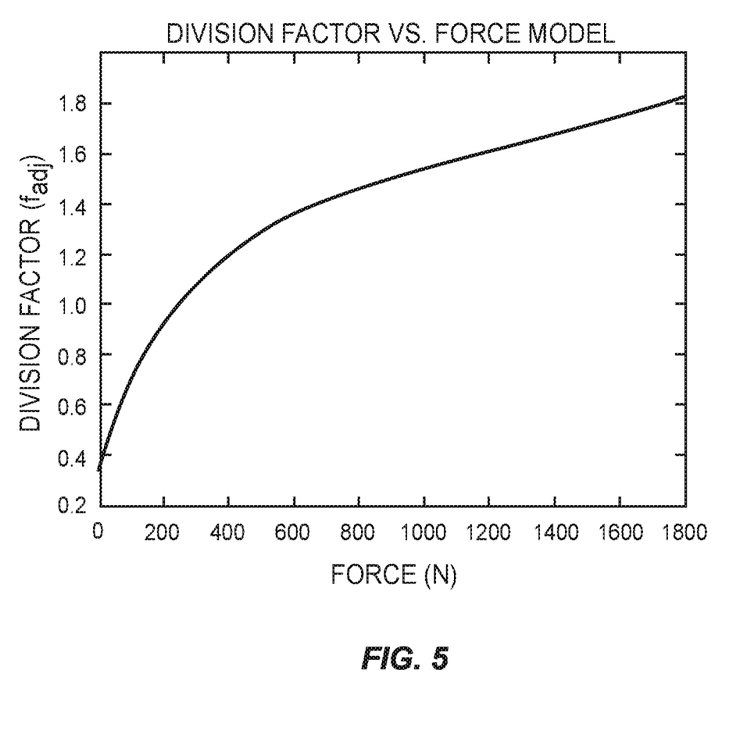
FIG. 5 is a graph illustrating a non-linear force conversion model according to one embodiment of the present disclosure.

FIG. 5 is a graph illustrating an exemplary relationship between the division factor discussed above and the total force. As shown, there is a non-linear relationship between the division factor and the force. The division factor may be used by the processing circuitry 44 as discussed above to determine an accurate total force as measured by the force sensors 26.

Figure 6:
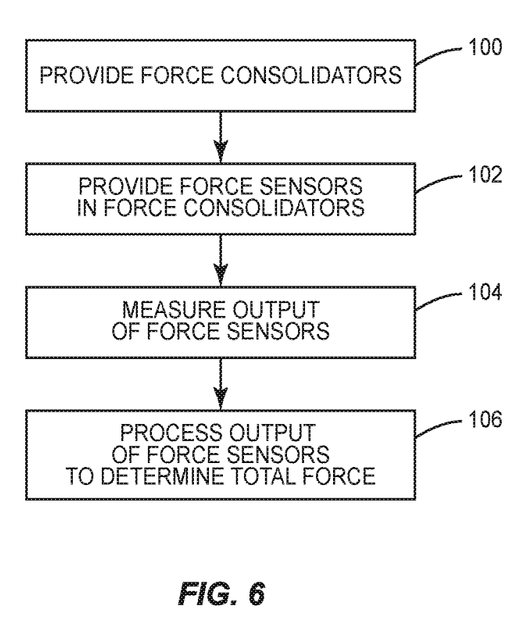
FIG. 6 is a flow diagram illustrating a method for measuring the force exerted between an object and a surface according to one embodiment of the present disclosure.

FIG. 6 is a flow chart illustrating a method for accurately measuring the total force exerted between an object and a surface according to one embodiment of the present disclosure. First, the force consolidators 24 are provided between the object and the surface (step 100). As discussed above, when the object is a foot and the surface is a walking surface, the force consolidators may be provided in a shoe. The force consolidators 24 allow the total force exerted by the object to be concentrated into a smaller surface area, which allows the total force to be easily measured. The force sensors 26 are provided in the force consolidators 24 (step 102). As discussed above, the force sensors 26 are provided to bisect two layers of the force consolidators 24 so that the force sensors measure the total force provided through the force consolidators 24. The output of the force sensors 26 is then measured (step 104). Finally, the output of the force sensors 26 is processed to determine a total force exerted by the object on the surface (step 106). As discussed above, the processing may involve applying a non-linear conversion model to the measurements form the force sensors 26 in order to determine the total force.

Those skilled in the art will recognize improvements and modifications to the preferred embodiments of the present disclosure. All such improvements and modifications are considered within the scope of the concepts disclosed herein and the claims that follow.

What is claimed is:

1. A method comprising:
providing a plurality of force consolidators on a wearable object, wherein the plurality of force consolidators is configured to reduce a surface area of the wearable object into a consolidated surface area such that forces exerted on the surface area are concentrated in the consolidated surface area;
providing a plurality of force sensors, wherein each one of the plurality of force sensors is provided edge-to-edge between an upper force consolidator layer and a lower force consolidator layer of a different one of the plurality of force consolidators;
measuring an output of the each one of the plurality of force sensors; and
processing the output of the each one of the plurality of force sensors to determine a total force exerted across the surface area of the wearable object.

2. The method of claim 1 wherein
each one of the plurality of force sensors measures an entirety of a force provided via the one of the plurality of force consolidators in which it is provided.

3. The method of claim 2 wherein each one of the plurality of force sensors bisects the upper force consolidator layer and the lower force consolidator layer of the one of the plurality of force consolidators in which it is provided.

4. The method of claim 1 wherein the wearable object is a shoe.

5. The method of claim 4 wherein the plurality of force consolidators reduces a total surface area along a bottom surface of the shoe normally in contact with the ground.

6. The method of claim 1 wherein the wearable object is a glove.

7. The method of claim 6 wherein the plurality of force consolidators reduces a total surface area along a bottom surface of the glove normally in contact with a held object.

8. The method of claim 1 wherein each one of the plurality of force sensors comprises a transducer configured to transduce a mechanical force into an electrical signal.

9. The method of claim 1 wherein processing the output of each one of the plurality of force sensors to determine the total force exerted across the surface area of the wearable object comprises applying a non-linear transform to the output of each one of the plurality of force sensors.

10. A wearable object comprising:
a plurality of force consolidators on the wearable object, each comprising an upper force consolidator layer and a lower force consolidator layer, wherein each one of the plurality of force consolidators reduces a surface area of the wearable object into a consolidated surface area such that forces exerted on the surface area are concentrated in the consolidated surface area;
a plurality of force sensors, each extending edge-to-edge between the upper force consolidator layer and the lower force consolidator layer in a different one of the plurality of force consolidators; and
force determination circuitry configured to process an output of the each one of the plurality of force sensors to determine a total force exerted across the surface area of the wearable object.

11. The wearable object of claim 10 wherein
each one of the plurality of force sensors measures an entirety of a force provided via the one of the plurality of force consolidators in which it is provided.

12. The wearable object of claim 11 wherein each one of the plurality of force sensors bisects the upper force consolidator layer and the lower force consolidator layer.

13. The wearable object of claim 10 wherein the wearable object is a shoe.

14. The wearable object of claim 13 wherein the plurality of force consolidators reduces a total surface area along a bottom surface of the shoe normally in contact with the ground.

15. The wearable object of claim 10 wherein the wearable object is a glove.

16. The wearable object of claim 15 wherein the plurality of force consolidators reduces a total surface area along a bottom surface of the glove normally in contact with a held object.

17. The wearable object of claim 10 wherein each one of the plurality of force sensors comprises a transducer configured to transduce a mechanical force into an electrical signal.

18. The wearable object of claim 10 wherein processing the output of each one of the plurality of force sensors to determine the total force exerted across the surface area of the wearable object comprises applying a non-linear transform to the output of each one of the plurality of force sensors.

19. The wearable object of claim 17 wherein each one of the plurality of force sensors comprises a resistive transducer that varies a resistance between a first electrode and a second electrode in proportion to a force applied thereto.

20. The wearable object of claim 17 wherein each one of the plurality of force sensors comprises a capacitive transducer that varies a capacitance between a first electrode and a second electrode in proportion to a force applied thereto.

* * * * *